(12) United States Patent
Moe

(10) Patent No.: US 8,784,651 B2
(45) Date of Patent: Jul. 22, 2014

(54) WATER SEPARATOR

(76) Inventor: Fridthjof Moe, Drøbak (NO)

(*) Notice: Subject to any disclaimer, the term of this patent is extended or adjusted under 35 U.S.C. 154(b) by 767 days.

(21) Appl. No.: 13/120,860

(22) PCT Filed: Sep. 26, 2008

(86) PCT No.: PCT/NO2008/000344
§ 371 (c)(1),
(2), (4) Date: May 12, 2011

(87) PCT Pub. No.: WO2010/036119
PCT Pub. Date: Apr. 1, 2010

(65) Prior Publication Data
US 2011/0233116 A1 Sep. 29, 2011

(51) Int. Cl.
B01D 35/14 (2006.01)
A61C 17/06 (2006.01)
B01D 29/00 (2006.01)

(52) U.S. Cl.
CPC ............ A61C 17/046 (2013.01); B01D 29/009 (2013.01); B01D 35/14 (2013.01)
USPC ........... 210/104; 210/136; 210/258; 210/406; 422/92; 422/95; 137/205; 137/396

(58) Field of Classification Search
CPC .................................................... A61C 17/046
USPC ..................................................... 433/92, 95
See application file for complete search history.

(56) References Cited

U.S. PATENT DOCUMENTS

| 3,017,886 | A | 1/1962 | Thompson |
| 3,768,478 | A | 10/1973 | Fertik et al. |
| 3,912,638 | A | 10/1975 | Beaubien |
| 4,293,300 | A | 10/1981 | Cattani |
| 4,564,374 | A | 1/1986 | Hofmann |
| 4,684,345 | A | 8/1987 | Cattani |
| 7,621,898 | B2 * | 11/2009 | Lalomia et al. ............... 604/319 |

FOREIGN PATENT DOCUMENTS

EP 0 387 774 A2 9/1990
WO WO 2006/043817 A1 4/2006

* cited by examiner

Primary Examiner — Terry Cecil
(74) Attorney, Agent, or Firm — Birch, Stewart, Kolasch & Birch, LLP

(57) ABSTRACT

A water separator for continuous separation of water, air and particles includes an inlet pipe, an outlet pipe, an upper chamber connected with a lower chamber, and a three-way valve located in an air connection pipe being adapted to establish a connection between the upper and lower chambers in a first position and closing the connection to the upper chamber and allowing atmospheric air to enter into the lower chamber in a second position. The upper chamber includes a coarse filter capturing particles from the liquid flow to the lower chamber. The water separator includes a main tank and a safety tank, which are connected through a connection pipe from the upper chamber in the main tank to the safety tank and through the air connection pipe from the lower chamber in the main tank to the safety tank. The inlet pipe is through the lid of the main tank.

5 Claims, 1 Drawing Sheet

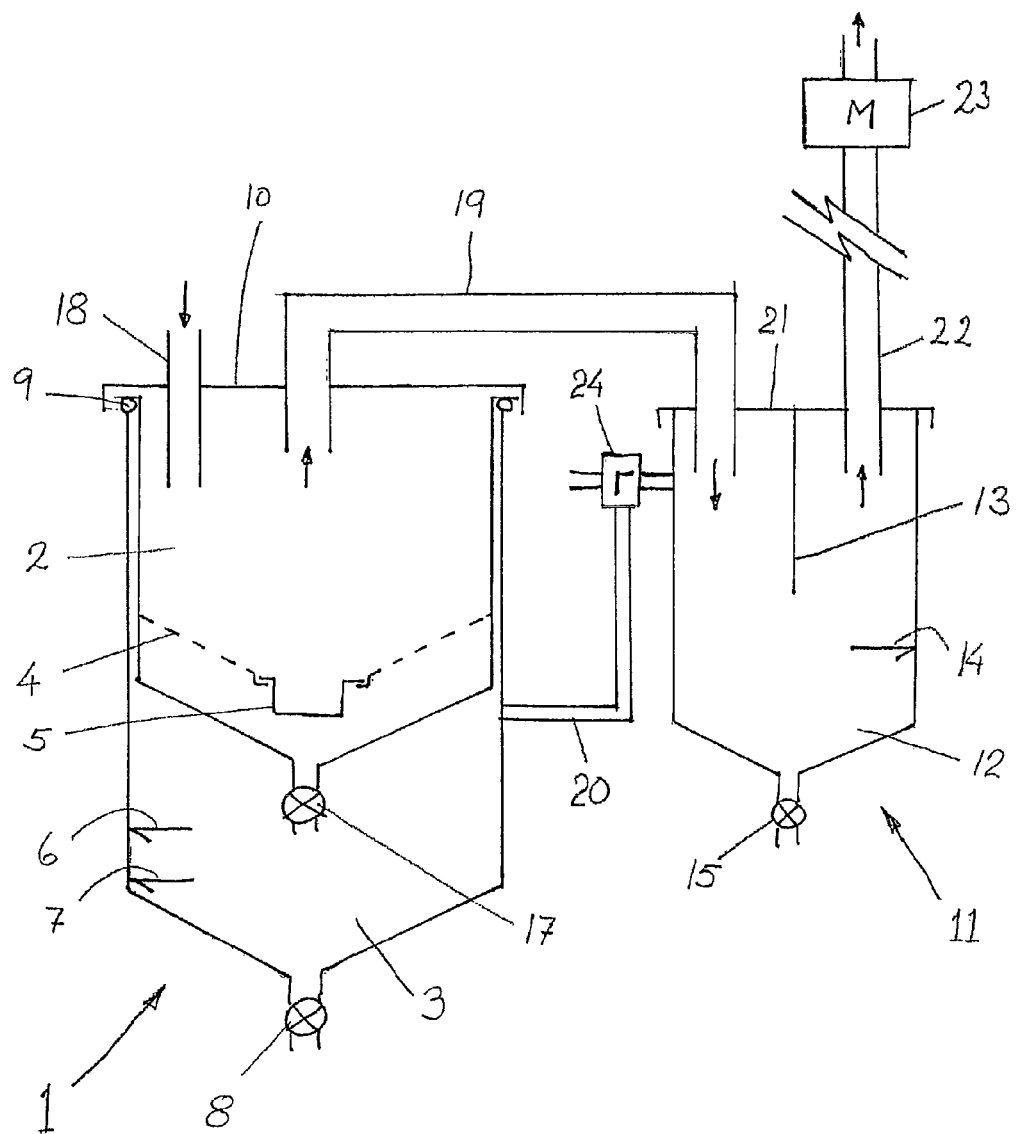

WATER SEPARATOR

FIELD OF THE INVENTION

The present invention is related to a water separator for continuous separation of water, air and particles.

BACKGROUND OF THE INVENTION

Separators of the above type are used by dentists, dental surgery as well as in other areas such as water absorbers, where the object is to separate air from water and particles which are sucked into a piping system.

Such apparatus is well known and in use by dentists sucking saliva from the mouth of patients during works in the oral cavity.

Some of the problems with known art is that the apparatus often need to be stopped because of the necessity of emptying the "waste-water" separator tank because it is full, irrespective of state of the operation. They are often rather voluminous and complex in their design which also complicate the cleaning maintenance.

In an attempt to overcome these problems a new design was introduced in the international application WO 2006/043817 by Fridthjof Moe. In this application a single waste-water separator tank, divided into two chambers, was used to solve some of the problems above. However, new features created new issues. The vacuum pump on top of the waste-water separator tank have a tendency to malfunction or be permanently damaged. The reason for this is the very high content of water, in the form of dense mist. The mist create water droplets in the vacuum motor/pump which in the end lead to that the vacuum motor fail. Another problem is that the drainpipe/valve in the lower chamber becomes clogged up and the waste-water separator tank do not empty. The vacuum pump will in the most favourable situation stop and not start again before someone has emptied the tank, or in worst case start to pull waste-water directly into the vacuum motor/pump. As to maintenance of the waste-water separator tank, the inlet pipe enter through the wall of the tank and this makes it cumbersome and time consuming to dismantle.

Further examples of known art can be found in U.S. Pat. Nos. 4,564,374 A, 4,293,300 A, 4,684,345 A and EP 0387774 A2.

SUMMARY OF THE INVENTION

It therefore is an object for the present application to provide an apparatus which reduces the chance for failure of the vacuum motor/pump and which at the same time provide a tank which is easy to maintain and thus provide a reliable and secure tool for waste-water separation. Above all it is an object to provide an apparatus which can work continuously without the need to stop the apparatus for emptying the tank.

The above objects are achieved with the waste-water separator tank according to the present invention as defined by the features stated in the claims.

BRIEF DESCRIPTION OF THE DRAWING

The drawing discloses schematically a vertical section of the apparatus according to the invention.

DETAILED DESCRIPTION OF THE INVENTION

The apparatus comprises two waste-water separator tanks, a main tank 1 and a safety tank 11.

The main tank 1 comprises of a lid 10, an upper chamber 2 and a lower chamber 3. The upper chamber 2 is created by putting a smaller tank inside the main tank 1. The upper edge of this smaller tank has a lip which rest on top of the upper edge of the main tank 1 or on a ridge (not shown) created on the wall inside the main tank 1. Between the outside wall of the smaller tank and the inside wall of the main tank 1 there exist at least one sealing element 9. The upper chamber 2 comprises a coarse filter 4 and an opening at the bottom/lowest end with a valve 17 controlling the flow out of the upper chamber 2. The coarse filter 4 can either rest on some ridges in the wall of the chamber or be fixed, either permanently or releasable. The filter 4 has an opening in the centre where upon a loose or releasable coarse filter cup 5 is placed. The lower chamber 3 comprises of at least one level switch 6,7 a check valve 8 controlling the liquid flow out of the lower chamber 3 and an outlet to an air connection pipe 20. Two pipes enters through the lid 10, one inlet pipe 18 and a connection pipe 19.

The safety tank 11 with an opening at the bottom/lowest end, comprises of a lid 21, at least one chamber 12 which is partly divided by a wall 13, at least one level switch 14, a check valve 15, at the bottom/lowest end, controlling the liquid flow out of the safety tank 11 and an outlet to the air connection pipe 20. Two pipes enters through the lid 21, the connection pipe 19 and an outlet pipe 22.

A mixture to be separated is guided into the inlet pipe 18 and may comprise water, air, dust, blood as well as residues of flesh from the mouth. The inlet pipe 18 is guiding the mixture of water and air against the cylindrical wall of the upper chamber 2 thereby allowing water, dust, blood and such to fall down, whereas the air is escaping upwardly through the connection pipe 19 through the lid of the main tank 1.

The mixture of water, dust, blood etc. passes through the coarse filter 4 which will capture the larger particles and allowing the smaller particles and liquid to pass through. The smaller particles and liquid will be collected at the bottom of the upper chamber and led through the opening and the valve 17 in the bottom of the upper chamber 2 and into the lower chamber 3.

In one embodiment the filter 4 is shaped as a cone with the narrow end pointing downwards with a hole in the middle. The hole is covered by a filter cup 5 which rest in the hole of the filter 4. Thus when any particles are stopped by the filter 4, they will be carried down to the filter cup where they will rest. Thus when the filter 4 need to be cleaned, it may be sufficient just to empty the filter cup, rather than dismantling the whole filter.

A suction motor/pump 23 is connected with the outlet pipe 22 on top of the safety tank 11. This suction motor/pump 23 will create an under pressure in the safety tank 11 and thus through the connection pipe 19, also in the upper chamber 2.

Between the main tank 1 and the safety tank 11 there is an air connection pipe 20 with a three way valve 24 connected to it. This arrangement will connect the lower chamber 3 with the safety tank 11 in normal position and thus the upper chamber 2 through the connection pipe 19. This will maintain the same under pressure in the upper chamber 2 as in the lower chamber 3.

The lower chamber 3 is normally closed at the bottom by the check valve 8, thereby allowing the lower chamber 3 to be filled up with water and possibly smaller particles having passed through the coarse air filter 4 and the valve 17.

When the lower chamber 3 is filled up to a specified level, a level switch 6 activates the three-way valve 24 to close the connection between the safety tank 11 and the lower chamber 3. This will let air into the lower chamber 3 and create a differential pressure over the valve 17. The valve 17 will then automatically close due to the under pressure in the upper chamber 2. The pressure in the lower chamber 2 will then return to atmospheric or higher pressure and release the check valve 8 which will open and drain the content of the lower chamber 3 until the water level in the lower chamber 3 reaches a lower level switch 7. This will then activate the three-way valve 24 for it to return to the normal position and thereby closing the air supply to the lower chamber 3 and connecting the under pressure of the safety tank 11 to the lower chamber 3.

When the same pressure is reached in the upper 2 and the lower 3 chambers, the valve 17 will open and waste-water which in the meantime has been collected in the upper chamber 2 will drain down into the lower chamber 3. The normal operation mode is then re-established as the safety tank 11 is connected with the lower chamber 3 through the three-way valve 24 and the air connection pipe 20. Due to the under pressure the check valve 8 at the bottom of the lower chamber 3 will close.

The process will then continue in an automatic manner allowing the lower chamber 3 to be emptied during a constant supply of water and mixture through the inlet pipe 18.

A level switch 14 is arranged in the safety tank 11. If the surface of the content in the upper chamber 2 rises to an undesired level during emptying of the lower chamber 3 the connection pipe 19 may start to suck water from the upper chamber 2 and feed the safety tank with waste-water rather than humid air. The level switch 14 will then deactivate the suction motor 13 and an audible and/or visible alarm will be given to indicate that the apparatus need attention. The purpose of the level switch 14 is to avoid the suction motor 23 to suck in water or highly humid air and thus fail or be permanently damaged. The check valve 15 in the bottom of the safety tank is working in the same manner as the check valve in the bottom of the main tank. When the suction motor 23 stop, any waste-water in the bottom of the safety tank will drain out as the under pressure disappear.

The invention claimed is:

1. A water separator for continuous separation of water, air and particles, said separator comprising:
   an inlet pipe configured to receive a mixture of water, air and particles simultaneously from several sources;
   an outlet pipe connected to a suction motor;
   an upper chamber connected with a lower chamber by a valve in the bottom of the upper chamber, a bottom of the lower chamber normally being closed by a check valve; and
   a three-way valve located in an air connection pipe being adapted to establish a connection between the upper and lower chambers in a first position and closing said connection to the upper chamber and allowing atmospheric air to enter into the lower chamber in a second position,
   wherein the upper chamber comprises a coarse filter capturing particles from the liquid flow to the lower chamber, wherein the water separator comprises two tanks, a main tank and a safety tank, which are connected through a connection pipe from the upper chamber in the main tank to the safety tank and through the air connection pipe from the lower chamber in the main tank to the safety tank,
   wherein the inlet pipe is through a lid of the main tank, and
   wherein the outlet pipe is through a lid of the safety tank, and wherein a bottom of the safety tank is normally closed by a check valve.

2. The water separator according to claim 1, wherein the lower chamber comprises a level switch adapted to place the three way valve in the second position when the water level in the lower chamber reaches the level switch.

3. The water separator according to claim 2, wherein the lower chamber comprises a lower level switch below the first level switch, being adapted to return the three way valve to the first position when the water level in the lower chamber reaches the lower level switch.

4. The water separator according to claim 3, wherein the safety tank comprises a level switch adapted to stop the suction motor and to give an alarm.

5. A method of controlling a water separator according to claim 4, where said level switch being activated by the water surface reaching said level switch causing the three-way valve to close the connection to the upper chamber and allowing atmospheric air to enter into the lower chamber, the valve in the upper chamber thereby closing due to the under pressure in the upper chamber through the safety tank, the check valve opening due to the atmospheric pressure in the lower chamber thereby allowing the content of the lower chamber to be drained until the surface of the content in the lower chamber reaches the lower level switch said switch activating the three-way valve to return to the first position for normal operation, wherein said level switch in the safety tank being activated by water surface reaching said level in the safety tank switch causing the suction motor to be stopped abruptly and an alarm signal being sent.

* * * * *